(12) United States Patent
Mangiardi et al.

(10) Patent No.: US 8,083,692 B2
(45) Date of Patent: Dec. 27, 2011

(54) LUMEN-MEASURING DEVICES AND METHOD

(75) Inventors: Eric K. Mangiardi, Charlotte, NC (US); Jason M. Reynolds, Charlotte, NC (US); Ulf R. Borg, Cornelius, NC (US); Tony D. Alexander, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 12/898,213

(22) Filed: Oct. 5, 2010

(65) Prior Publication Data

US 2011/0082392 A1    Apr. 7, 2011

Related U.S. Application Data

(62) Division of application No. 10/618,223, filed on Jul. 11, 2003.

(51) Int. Cl.
*A61B 5/103* (2006.01)
*A61B 1/00* (2006.01)

(52) U.S. Cl. .......................................... 600/587; 33/512

(58) Field of Classification Search .................. 600/587, 600/588, 591, 593; 33/485, 511, 512, 542, 33/544, 548, 555.1
See application file for complete search history.

(56) References Cited

U.S. PATENT DOCUMENTS

| | | |
|---|---|---|
| 3,196,876 A | 7/1965 | Roberts et al. |
| 4,016,867 A | 4/1977 | King et al. |
| 4,204,548 A | 5/1980 | Kurz |
| 4,362,167 A | 12/1982 | Nicolai et al. |
| 4,489,732 A | 12/1984 | Hasson |
| 4,606,330 A | 8/1986 | Bonnet |
| 4,893,623 A | 1/1990 | Rosenbluth |
| 4,972,584 A | 11/1990 | Baumann |
| 5,010,892 A | 4/1991 | Colvin et al. |
| 5,019,085 A | 5/1991 | Hillstead |
| 5,159,920 A | 11/1992 | Condon et al. |
| 5,249,585 A | 10/1993 | Turner et al. |
| 5,320,617 A | 6/1994 | Leach |
| 5,356,382 A | 10/1994 | Picha et al. |
| 5,409,453 A | 4/1995 | Lundquist et al. |
| 5,514,093 A | 5/1996 | Ellis et al. |
| 5,549,644 A | 8/1996 | Lundquist et al. |
| 5,565,211 A | 10/1996 | Rossi |
| 5,588,949 A | 12/1996 | Taylor et al. |
| 5,601,591 A | 2/1997 | Edwards et al. |
| 5,603,698 A | 2/1997 | Roberts et al. |

(Continued)

FOREIGN PATENT DOCUMENTS

DE           2840633           3/1980

(Continued)

OTHER PUBLICATIONS

EP Communication and Supplementary Partial European Search Report for EP Application No. 04 77 8005, mailed Apr. 14, 2009.

(Continued)

*Primary Examiner* — Max Hindenburg
*Assistant Examiner* — Emily Lloyd
(74) *Attorney, Agent, or Firm* — Stoel Rives LLP

(57) ABSTRACT

The present invention provides a lumen measuring device and method that allows the user to calculate the exact length and diameter of a suitable interventional prosthesis as well as the height and length of stenosis during the same exploratory procedure.

14 Claims, 15 Drawing Sheets

U.S. PATENT DOCUMENTS

| | | | |
|---|---|---|---|
| 5,667,522 A | 9/1997 | Flomenblit et al. | |
| 5,746,692 A | 5/1998 | Bacich et al. | |
| 5,752,522 A * | 5/1998 | Murphy | 600/587 |
| 5,782,838 A | 7/1998 | Beyar et al. | |
| 5,817,102 A | 10/1998 | Johnson et al. | |
| 5,824,058 A | 10/1998 | Ravenscroft et al. | |
| 5,833,694 A | 11/1998 | Poncet | |
| 5,902,333 A | 5/1999 | Roberts et al. | |
| 5,919,147 A | 7/1999 | Jain | |
| 5,984,964 A | 11/1999 | Roberts et al. | |
| 6,019,778 A | 2/2000 | Wilson et al. | |
| 6,033,359 A | 3/2000 | Doi | |
| 6,066,104 A | 5/2000 | Dao et al. | |
| 6,084,941 A | 7/2000 | Stenstrom | |
| 6,086,528 A | 7/2000 | Adair | |
| 6,162,231 A | 12/2000 | Mikus et al. | |
| 6,302,906 B1 | 10/2001 | Goicoechea et al. | |
| 6,322,586 B1 | 11/2001 | Monroe et al. | |
| 6,325,790 B1 | 12/2001 | Trotta | |
| 6,369,355 B1 | 4/2002 | Saunders | |
| 6,375,676 B1 | 4/2002 | Cox | |
| 6,395,007 B1 | 5/2002 | Bhatnagar et al. | |
| 6,427,351 B1 | 8/2002 | Matthews et al. | |
| 6,450,976 B2 | 9/2002 | Korotko et al. | |
| 6,450,977 B1 | 9/2002 | Baxter-Jones | |
| 6,451,025 B1 | 9/2002 | Jervis | |
| 6,517,569 B2 | 2/2003 | Mikus et al. | |
| 6,569,085 B2 | 5/2003 | Kortenbach et al. | |
| 6,623,491 B2 | 9/2003 | Thompson | |
| 6,656,214 B1 | 12/2003 | Fogarty et al. | |
| 6,663,660 B2 | 12/2003 | Dusbabek et al. | |
| 6,663,880 B1 | 12/2003 | Roorda et al. | |
| 6,669,716 B1 | 12/2003 | Gilson et al. | |
| 6,669,718 B2 | 12/2003 | Besselink | |
| 6,669,720 B1 | 12/2003 | Pierce | |
| 6,673,101 B1 | 1/2004 | Fitzgerald et al. | |
| 6,676,692 B2 | 1/2004 | Rabkin et al. | |
| 6,676,693 B1 | 1/2004 | Belding et al. | |
| 6,689,157 B2 | 2/2004 | Madrid et al. | |
| 6,695,809 B1 | 2/2004 | Lee | |
| 6,695,812 B2 | 2/2004 | Estrada et al. | |
| 6,695,862 B2 | 2/2004 | Cox et al. | |
| 6,699,274 B2 | 3/2004 | Stinson | |
| 6,699,277 B1 | 3/2004 | Freidberg et al. | |
| 6,702,849 B1 | 3/2004 | Dutta et al. | |
| 6,702,850 B1 | 3/2004 | Byun et al. | |
| 6,712,771 B2 | 3/2004 | Haddock et al. | |
| 6,723,071 B2 | 4/2004 | Gerdts et al. | |
| 6,723,113 B1 | 4/2004 | Shkolnik | |
| 6,726,712 B1 | 4/2004 | Raeder-Devens et al. | |
| 6,733,521 B2 | 5/2004 | Chobotov et al. | |
| 6,736,828 B1 | 5/2004 | Adams et al. | |
| 6,743,219 B1 | 6/2004 | Dwyer et al. | |
| 6,746,423 B1 | 6/2004 | Wantink | |
| 6,749,627 B2 | 6/2004 | Thompson et al. | |
| 6,752,819 B1 | 6/2004 | Brady et al. | |
| 6,752,825 B2 | 6/2004 | Eskuri | |
| 6,755,855 B2 | 6/2004 | Yurek et al. | |
| 6,761,703 B2 | 7/2004 | Miller et al. | |
| 6,761,708 B1 | 7/2004 | Chiu et al. | |
| 6,761,733 B2 | 7/2004 | Chobotov et al. | |
| 6,773,446 B1 | 8/2004 | Dwyer et al. | |
| 6,773,447 B2 | 8/2004 | Laguna | |
| 6,773,448 B2 | 8/2004 | Kusleika et al. | |
| 6,780,182 B2 | 8/2004 | Bowman et al. | |
| 6,780,199 B2 | 8/2004 | Solar et al. | |
| 6,790,220 B2 | 9/2004 | Morris et al. | |
| 6,790,223 B2 | 9/2004 | Reever | |
| 6,800,081 B2 | 10/2004 | Parodi | |
| 6,802,846 B2 | 10/2004 | Hauschild et al. | |
| 6,802,849 B2 | 10/2004 | Blaeser et al. | |
| 6,808,529 B2 | 10/2004 | Fulkerson | |
| 7,234,468 B2 | 6/2007 | Johnson et al. | |
| 2002/0161425 A1 | 10/2002 | Hemerick et al. | |
| 2002/0183763 A1 | 12/2002 | Callol et al. | |
| 2003/0120171 A1 | 6/2003 | Diamantopoulos et al. | |
| 2003/0144671 A1 | 7/2003 | Brooks et al. | |
| 2006/0064039 A1 | 3/2006 | Griego et al. | |

FOREIGN PATENT DOCUMENTS

| | | |
|---|---|---|
| DE | 3231863 | 3/1984 |
| DE | 41 37 751 | 11/1991 |
| EP | 0516189 | 12/1992 |
| JP | 11009573 | 6/1997 |
| JP | 2000-506033 | 5/2000 |
| JP | 2001-299932 | 10/2001 |
| WO | WO 97/14456 | 4/1997 |
| WO | WO 97/40739 | 11/1997 |
| WO | WO 99/56612 | 11/1999 |
| WO | WO 02/083038 | 10/2002 |
| WO | WO 02/64019 | 11/2002 |

OTHER PUBLICATIONS

PCT Notification of Transmittal of the International Search Report, PCT International Search Report mailed Jun. 3, 2005 for PCT/US04/22256 (Filed Jul. 9, 2004).
Office Action dated Jun. 22, 2010 for U.S. Appl. No. 11/252,363.
Office Action dated Nov. 25, 2009 for U.S. Appl. No. 11/252,363.
Office Action dated Jun. 23, 2009 for U.S. Appl. No. 11/252,363.
Office Action dated Jan. 9, 2009 for U.S. Appl. No. 11/252,363.
Response to Office Action dated Apr. 22, 2010 for U.S. Appl. No. 10/618,223.
Office Action dated Jan. 22, 2010 for U.S. Appl. No. 10/618,223.
Response to Office Action dated Dec. 11, 2008 for U.S. Appl. No. 10/618,223.
Office Action dated Oct. 14, 2008 for U.S. Appl. No. 10/618,223.
Response to Office Action dated Mar. 27, 2008 for U.S. Appl. No. 10/618,223.
Office Action dated Nov. 28, 2007 or U.S. Appl. No. 10/618,223.
Response to Office Action dated Sep. 11, 2007 for U.S. Appl. No. 10/618,223.
Office Action dated Jun. 12, 2007 for U.S. Appl. No. 10/618,223.
Response to Office Action dated Mar. 26, 2007 for U.S. Appl. No. 10/618,223.
Office Action dated Oct. 26, 2006 for U.S. Appl. No. 10/618,223.
Response to Office Action dated Jun. 15, 2006 for U.S. Appl. No. 10/618,223.
Office Action dated Mar. 16, 2006 for U.S. Appl. No. 10/618,223.
Response to Office Action dated Jan. 20, 2006 for U.S. Appl. No. 10/618,223.
Office Action dated Oct. 14, 2005 for U.S. Appl. No. 10/618,223.
Response to Office Action dated Aug. 3, 2005 for U.S. Appl. No. 10/618,223.
Response to Office Action dated May 17, 2005 for U.S. Appl. No. 10/618,223.
Office Action dated Feb. 17, 2005 for U.S. Appl. No. 10/618,223.
Response to Office Action dated Mar. 25, 2010 for U.S. Appl. No. 11/252,363.
Response to Office Action dated Sep. 9, 2009 for U.S. Appl. No. 11/252,363.
Response to Office Action dated Apr. 9, 2009 for U.S. Appl. No. 11/252,363.
Advisory Action dated Jan. 28, 2009 for U.S. Appl. No. 10/618,223.
Appeal Brief dated May 4, 2009 for U.S. Appl. No. 10/618,223.
Appeal Brief dated Jun. 8, 2009 for U.S. Appl. No. 10/618,223.
Examiners Answer to Appeal Brief dated Sep. 24, 2009 for U.S. Appl. No. 10/618,223.
Reply Brief dated Oct. 2, 2009 for U.S. Appl. No. 10/618,223.
Miscellaneous Communication dated Oct. 14, 2009 for U.S. Appl. No. 10/618,223.
Request for Continued Examination dated Nov. 24, 2009 for U.S. Appl. No. 10/618,223.
Non-Compliant Amendment dated Apr. 1, 2011 for U.S. Appl. No. 10/618,223.
Interview Summary dated Jun. 28, 2010 for U.S. Appl. No. 10/618,223.
Supplemental Amendment dated Jun. 28, 2010 for U.S. Appl. No. 10/618,223.
Supplemental Amendment dated Sep. 7, 2010 for U.S. Appl. No. 10/618,223.
Examination Interview Summary dated Sep. 17, 2010 for U.S. Appl. No. 10/618,223.
2001 Transcatheter Cardiovascular Therapeutics, TCT-95, pp. 38G-39G; The American Journal of Cardiology, Sep. 11, 2001 TCT Abstracts.

* cited by examiner

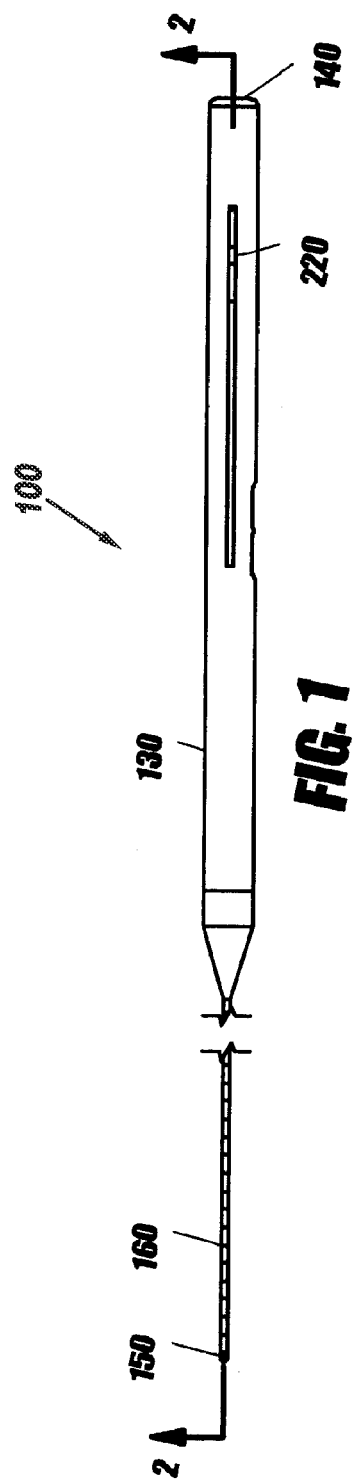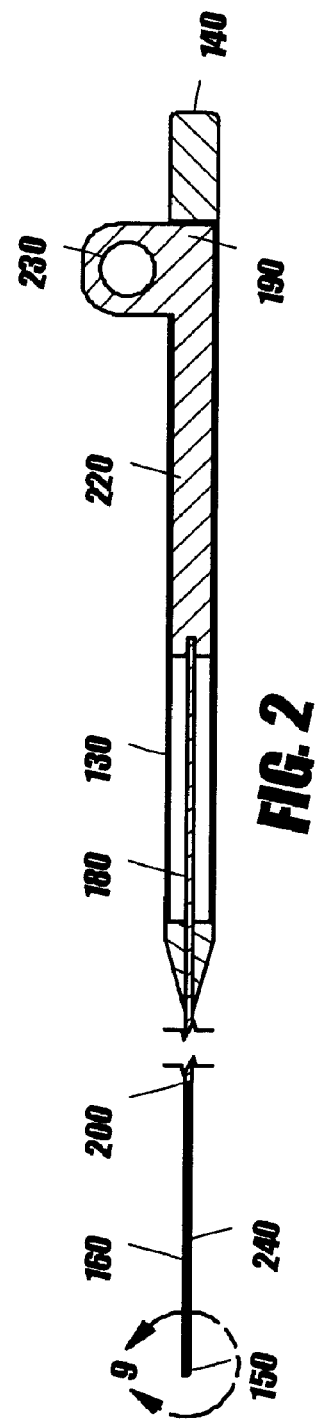

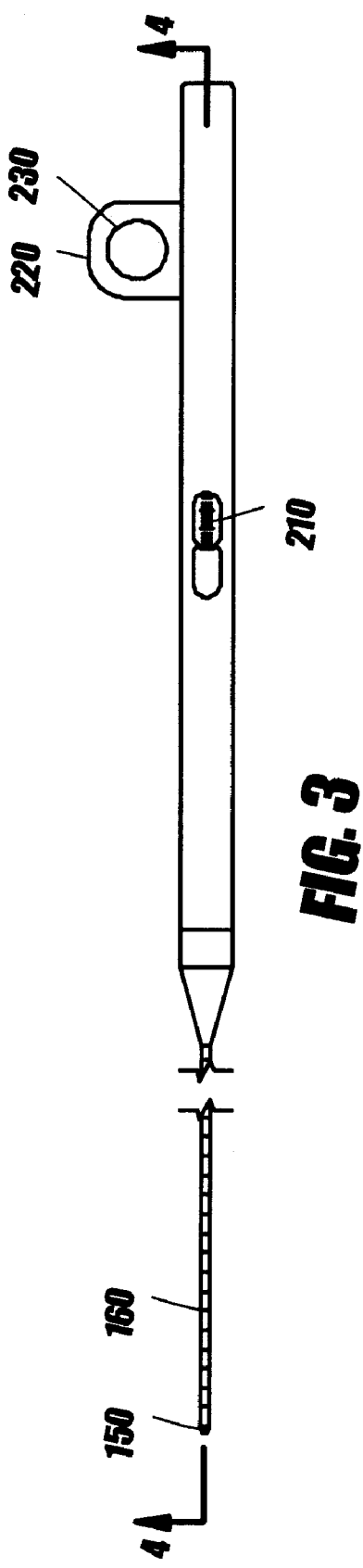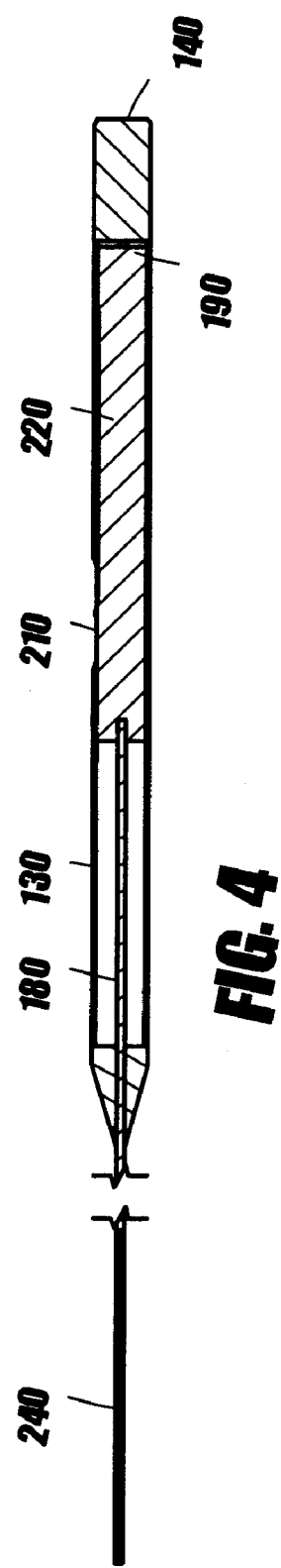

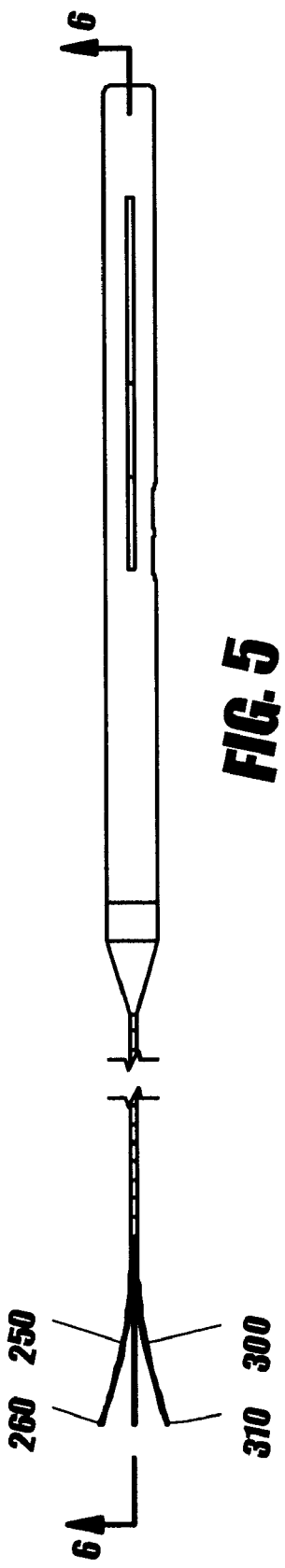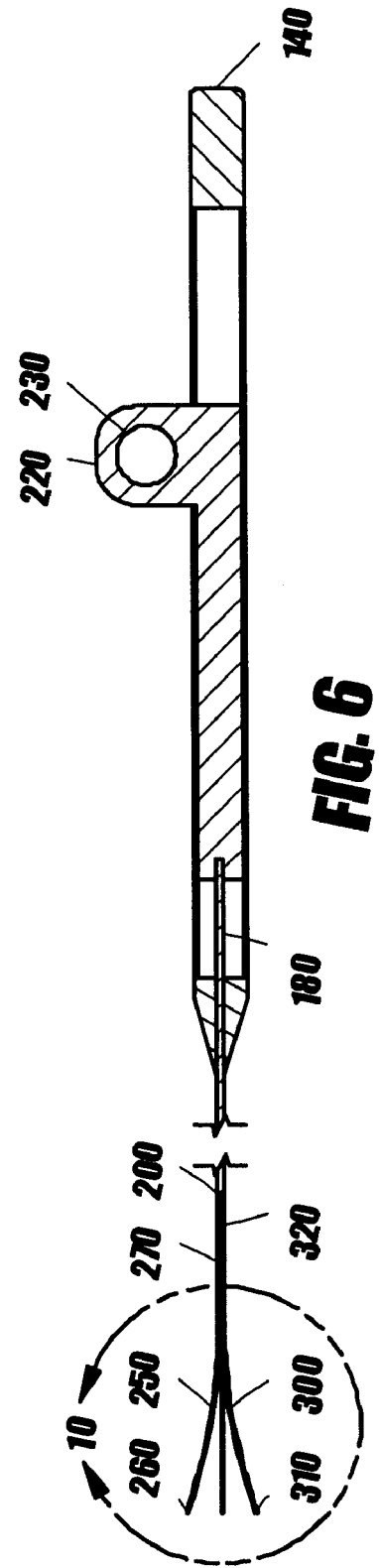

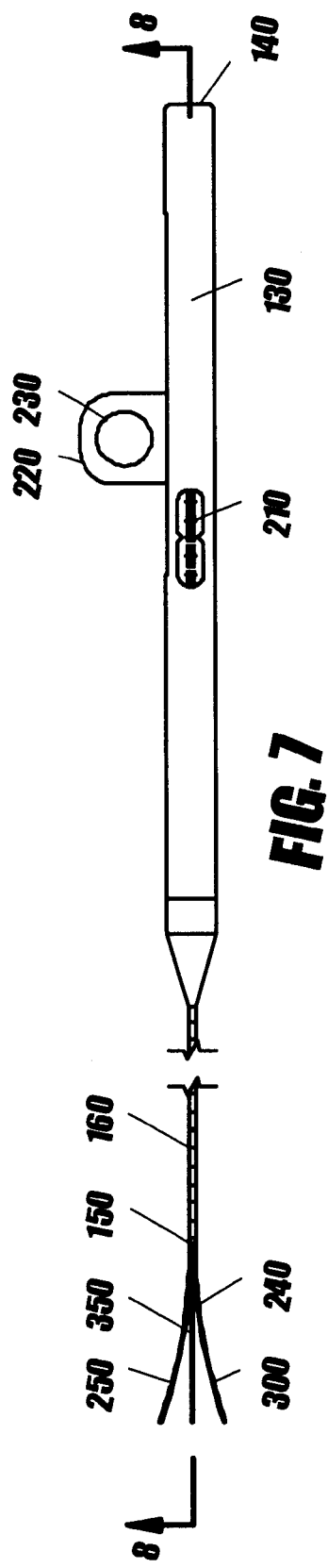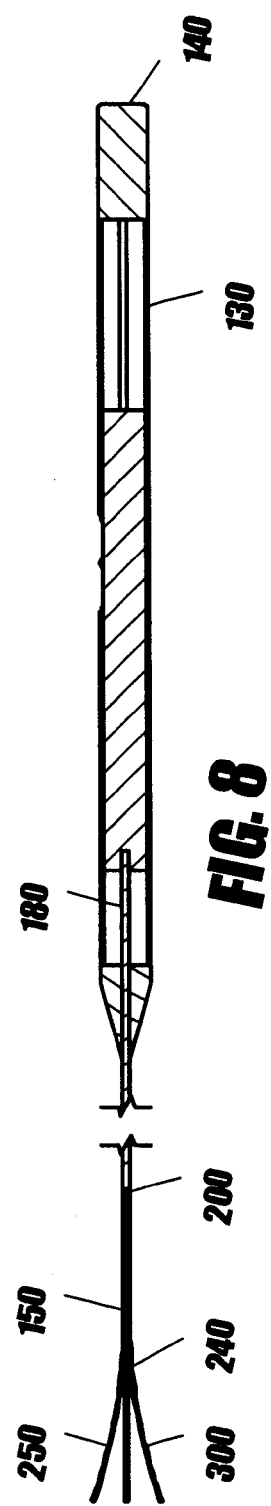

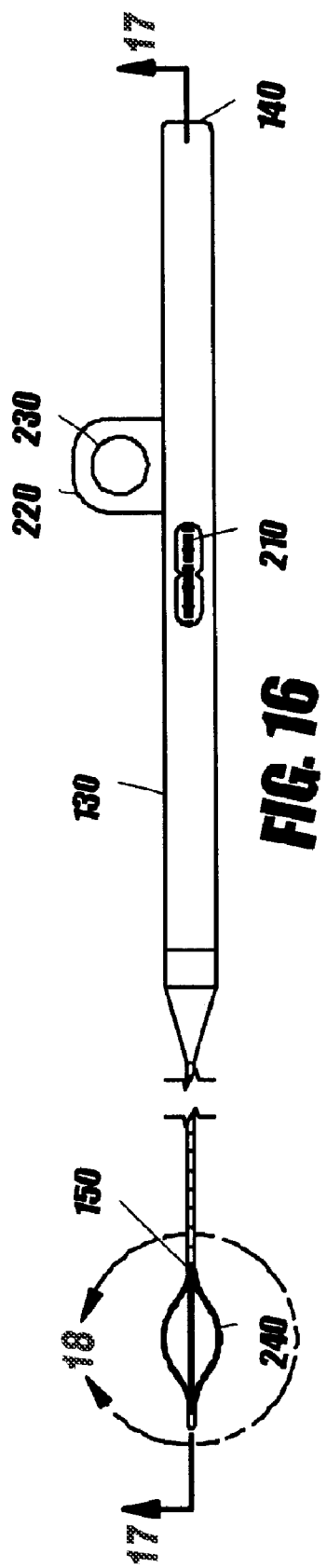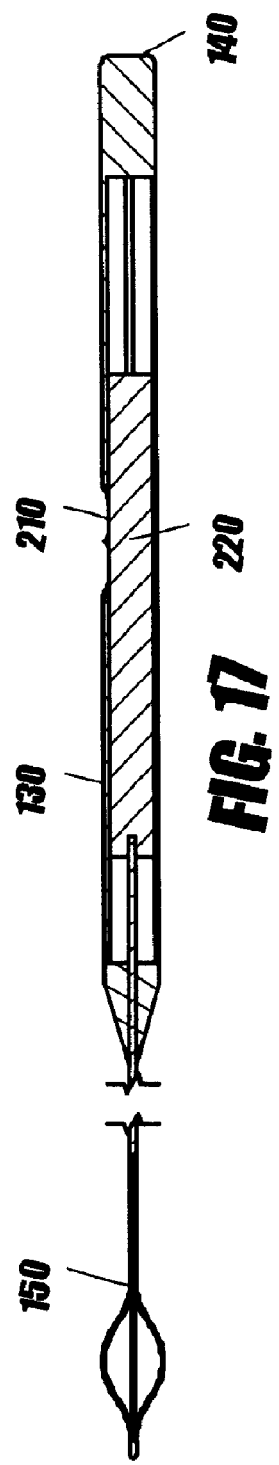

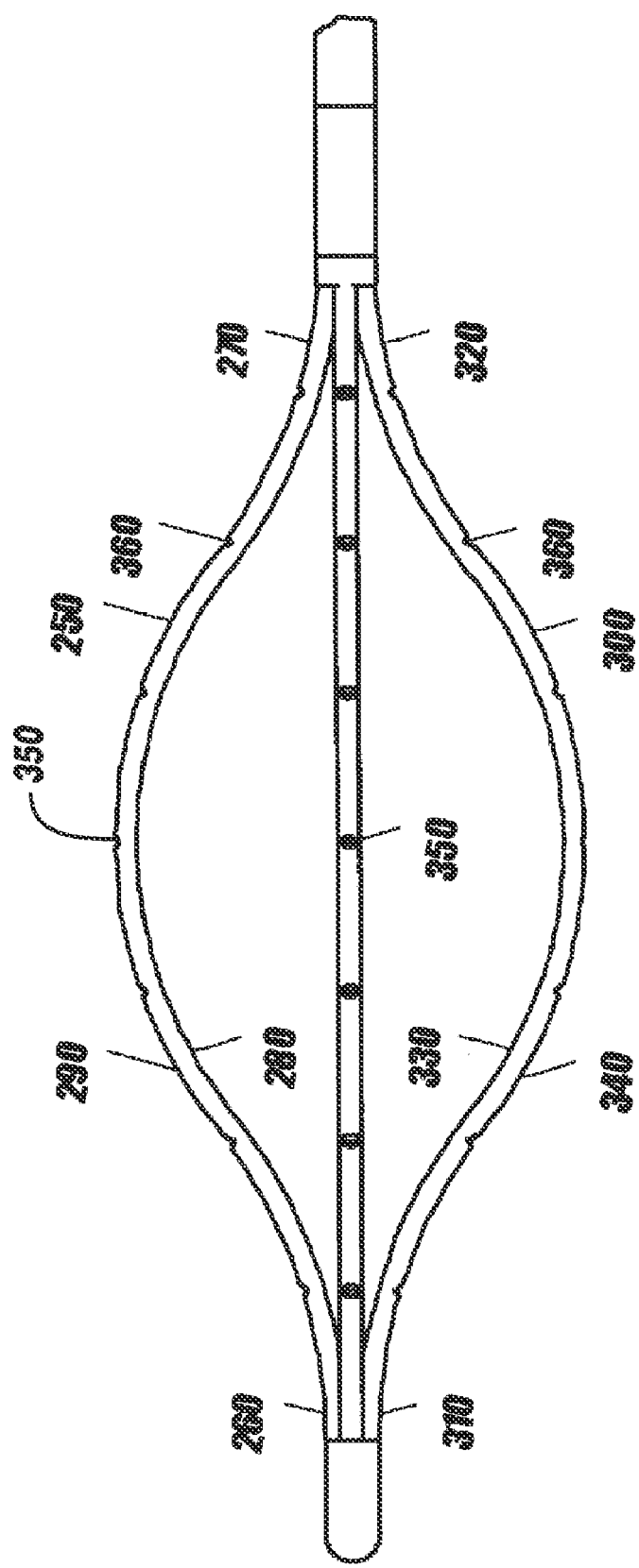

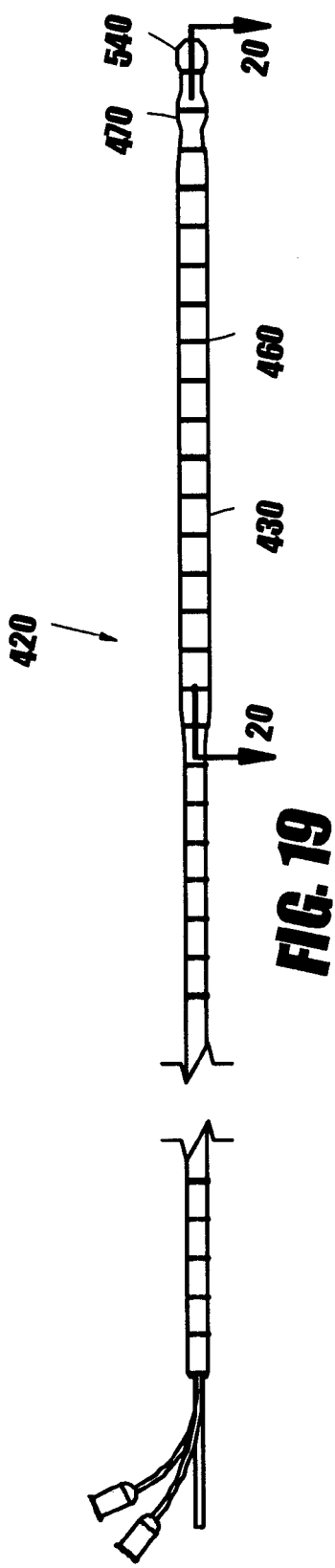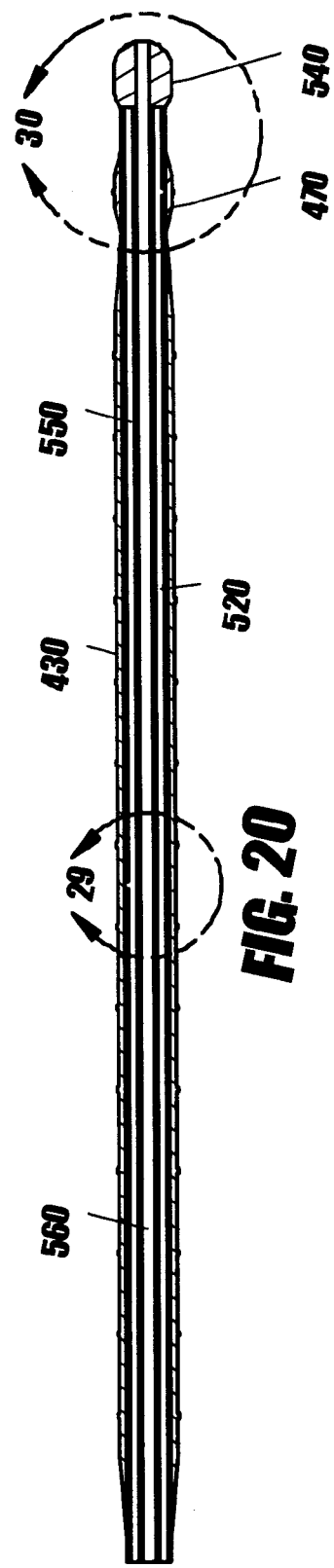
FIG. 19
FIG. 20

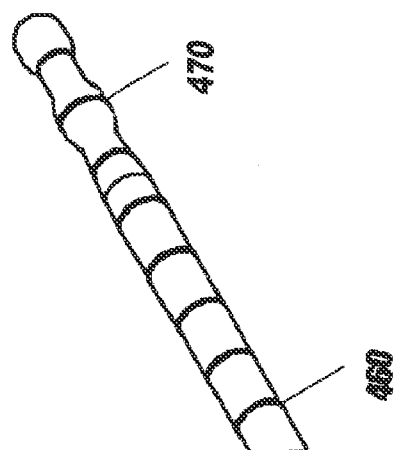
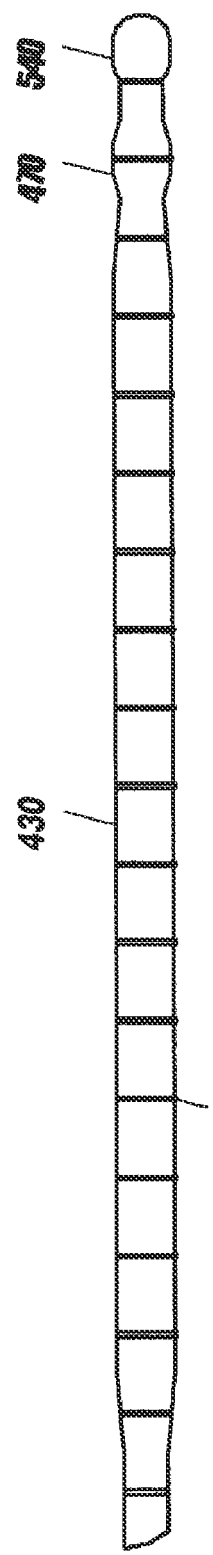

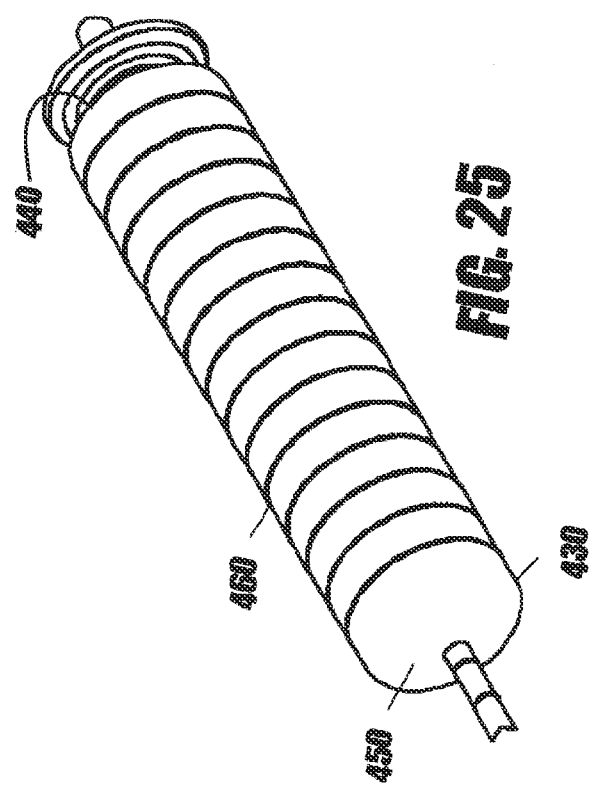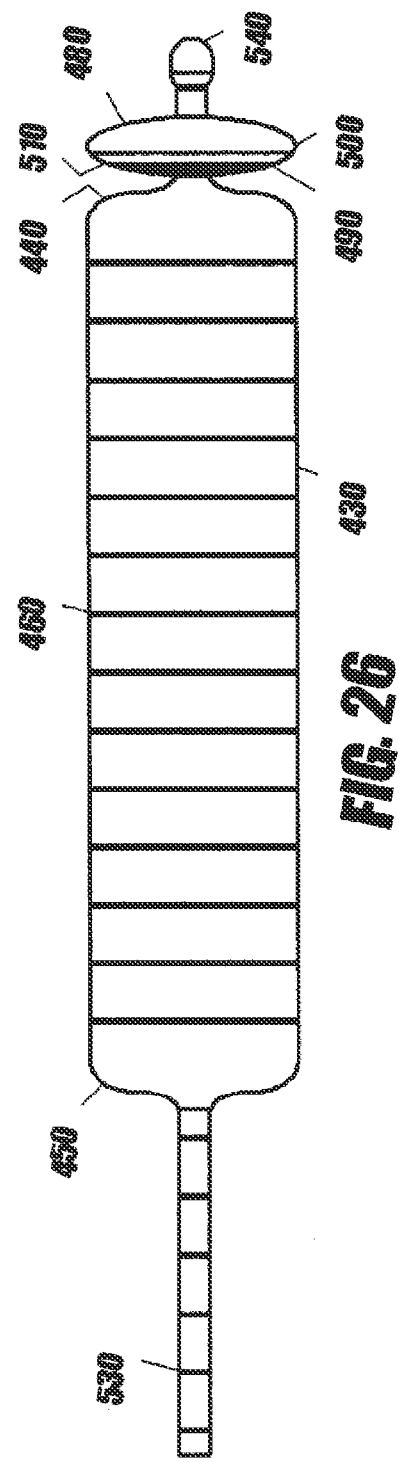

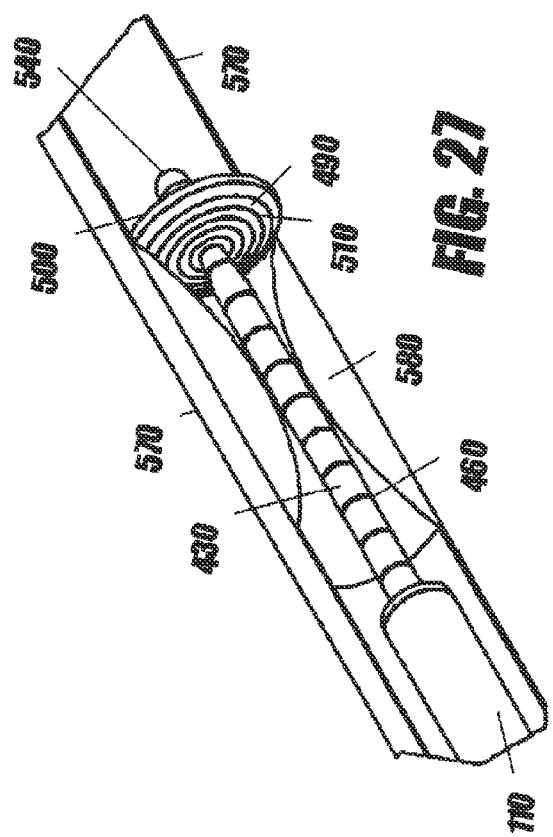
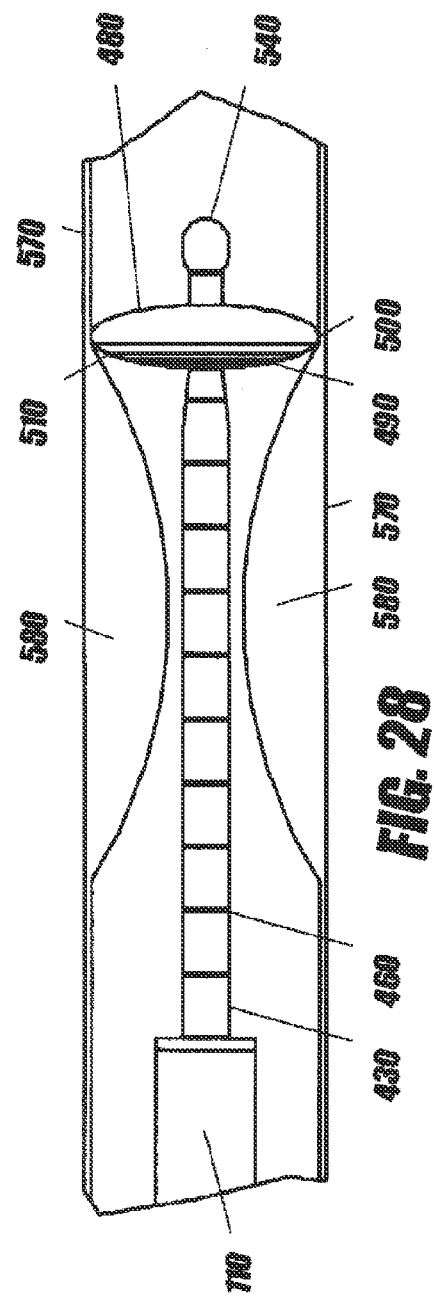

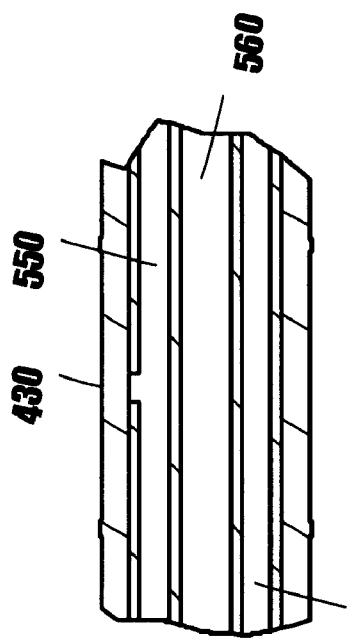
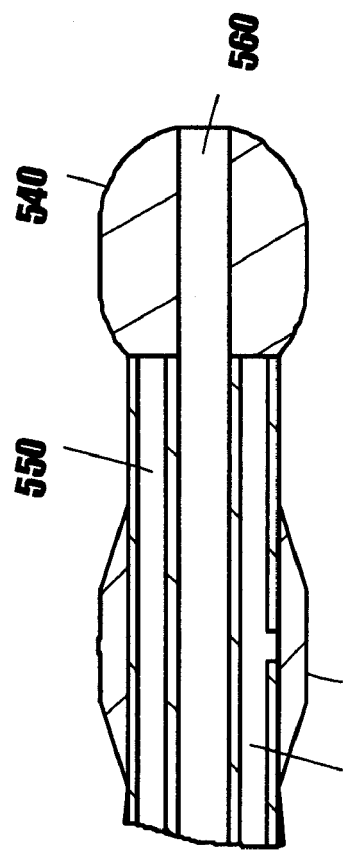

LUMEN-MEASURING DEVICES AND METHOD

CROSS REFERENCE TO RELATED APPLICATIONS

This patent application is a divisional of now pending U.S. patent application Ser. No. 10/618,223, entitled LUMEN-MEASURING DEVICES AND METHOD, filed on Jul. 11, 2003, which is fully incorporated by reference herein.

FIELD OF THE INVENTION

The present invention relates to measurement devices and methods and more particularly, to devices and methods of measuring the internal diameter of a lumen of a patient and the dimensions of luminal imperfection.

BACKGROUND OF THE INVENTION

Physicians involved in therapy in general and interventional cardiology and interventional radiology in particular have been attempting to find a way to deal with occluded (so called "stenotic") coronary arteries (among other blood vessels, various tubular conduits and similar structures). Additionally, the vessel diameter, as often measured using electronic calipers ('imaging' mode), and the frequency shift ('Doppler' mode) are of prime importance in determining the mean flow rate through a vessel and both must be accurately known. Unfortunately, methods of obtaining luminal dimensions are different based on the type of inquiry; the physicians interested in interventional treatment of stenosis have approached the problem differently than those interested in determining mean flow rate through a vessel.

Interventional radiologists interested in treatment of stenosis have focused attention principally on the topology of the stenosis almost to the exclusion of other important factors. Of principal importance is the identification of stent length as a risk factor for restenosis. The usual method of choosing stent size relies on visual estimation from the angiogram. Like many practitioners interested in this area the goal has been to assess the value of an objective means of determining stent length. In one instance, a calibrated guide wire (sold under the trademark ATW® Marker Wire; Cordis Corporation) is used as a measurement tool. J. P. Reilly et al. Use of ATW Marker Wire to Guide Choice of Stent Length, Am J Cardiol 2001; 88 (suppl 5A).

The theory behind this and other studies is that choice of appropriate endoluminal revascularization device (e.g., balloon angioplasty, atherectomy, laser recanalization, stents, etc) is a function of stenosis topology. Though excessive length of endoluminal revascularization devices can lead to migration and restenosis, a principal limitation of this analysis is that there are equally important risk factors associated with vessel diameter. Many practitioners pay more care in determining appropriate stent length than expanded stent diameter. As a rule of thumb, physicians generally employ a stent that is one to two sizes larger than the estimated lumen diameter. This practice in and of itself can lead to tissue granulation and further vessel damage.

Practitioners interested in hemodynamics or patency of vessels, defined as continued flow through the treated segment, not necessarily the absence of recurrent stenosis, use alternative tools to measure lumen diameter for purposes of determining the extent of flow there through. Most frequently, imaging tests such as CT Scans are used to assist with dimensional calculations. As a result, no apparatus has been developed that allows for accurate in situ measurement of treated or target tissue for purposes of evaluating patency and/or providing interventional prosthesis.

Therefore, there is an existing need for an accurate method of measuring both stenosis topography as well as luminal dimensions so that the precise interventional prosthesis may be employed. In particular, there is a need for a single device that can measure the width and height of a stenosis while also measuring the diameter of lumen at both healthy and stenotic regions.

SUMMARY OF EXEMPLARY EMBODIMENTS

It is a principal object in accordance with the present invention to provide a device capable of measuring the topology of a stenosis. In the furtherance of this and other objectives, a preferred embodiment of the present invention provides a measuring means that is disposable about, distal and proximal a stenosis for measuring the dimensions of the tissue in those locations.

Yet another objective in accordance with a preferred embodiment of the present invention is to provide a device that is suitable for measuring the working diameter of both healthy and diseased lumen for purposes of accurately determining the dimensions of an appropriate interventional prosthesis.

Still another objective of a preferred embodiment in accordance with the present invention is to provide a lumen measuring device and method that allows the user to calculate the exact length and diameter of a suitable interventional prosthesis as well as the height and length of a stenosis during the same exploratory procedure.

It is another objective in accordance with the present invention to provide a lumen-measuring device configured to be introduced into the working channel of a suitable anatomically correct optical scope. In the furtherance of this and other objectives, and provided by way of non-limiting example only, a device in accordance with the present invention that is used for nonvascular indications in general and pulmonary indications in particular may be suitably configured for use in the working channel of a bronchoscope. It is envisioned that the optical instrument chosen will be a function of the general vascular/nonvascular decision, anatomical location, and physician preference.

Further objectives, features and advantages of the invention will be apparent from the following detailed description taken in conjunction with the accompanying drawings.

BRIEF DESCRIPTION OF THE DRAWINGS

FIG. 1 is an aerial perspective view of an exemplary lumen-measuring delivery device in accordance with the present invention.

FIG. 2 is a side cross sectional view of an exemplary lumen delivery device of FIG. 1, along lines 2-2.

FIG. 3 is a side perspective view of the lumen-measuring device of FIG. 1, showing a measurement indicator through the exterior lumen.

FIG. 4 is a bottom cross sectional view of the lumen-measuring device of FIG. 3, along lines 4-4.

FIG. 5 is an aerial perspective view of an exemplary lumen-measuring delivery device in accordance with the present invention, showing the measurement assembly distally extended.

FIG. 6 is a side cross sectional view of an exemplary lumen delivery device of FIG. 5, along lines 6-6.

FIG. 7 is a side perspective view of the lumen-measuring device of FIG. 5, showing a measurement indicator through the exterior lumen.

FIG. 8 is a bottom cross sectional view of the lumen-measuring device of FIG. 7, along lines 8-8.

FIG. 16 is a side perspective view of an open measurement configuration of an alternative lumen-measuring device embodiment showing a measurement indicator through the exterior lumen.

FIG. 17 is a bottom cross-sectional view of the alternative lumen-measuring device of FIG. 16, showing the legs in the open measuring configuration.

FIG. 18 is a side perspective view of the measurement assembly of the alternative lumen-measuring device of FIG. 16, showing the legs in the open measuring configuration.

FIG. 19 is a side perspective view of an exemplary lumen-measuring device, wherein the measurement assembly comprises a dilation balloon, a diameter measurement balloon and measurement markers.

FIG. 20 is a cross sectional view of the lumen-measuring device of FIG. 19, showing the internal conduits that feed the respective balloons, along lines 20-20.

FIG. 21 is a perspective view of the measuring portion of the lumen-measuring device of FIG. 19, showing the measurement markers on the dilation balloon in the uninflated configuration.

FIG. 22 is a side view of the measuring portion of the lumen-measuring device of FIG. 19, showing the measurement markers on the dilation balloon in the uninflated configuration.

FIG. 25 is a perspective view of the measuring portion of the lumen-measuring device of FIG. 19, showing the measurement markers on the dilation and diameter measurement balloons in the inflated configuration.

FIG. 26 is a side view of the measuring portion of the lumen-measuring device of FIG. 19, showing the measurement markers on the dilation and diameter measurement balloons in the inflated configuration.

FIG. 27 is a perspective view of an exemplary lumen-measuring device of FIG. 19, indicated for nonvascular lumen, showing the lumen-measuring device disposed within the working channel of a bronchoscope, wherein the measurement assembly comprises a dilation balloon about a stenosis, a diameter measurement balloon which is in the inflated configuration and measurement markers.

FIG. 28 is a side view of an exemplary lumen-measuring device of FIG. 19, indicated for a nonvascular lumen, showing the lumen-measuring device disposed within the working channel of a bronchoscope, wherein the measurement assembly comprises a dilation balloon about a stenosis, a diameter measurement balloon which is in the inflated configuration and measurement markers.

FIG. 29 is a cross sectional view of the co-extruded conduits, of FIG. 20, showing an inflation channel along lines 29-29.

FIG. 30 is a side cross sectional view of the co-extruded conduits, of FIG. 20, showing an inflation channel along lines 30-30.

DETAILED DESCRIPTION OF THE PREFERRED EMBODIMENTS

A preferred embodiment in accordance with the present invention provides a lumen measuring device and method that allows the user to calculate the exact length and diameter of a suitable interventional prosthesis as well as the height and length of a stenosis during the same exploratory procedure. In the furtherance of this and other objectives, an exemplary device is capable of measuring the topology of a stenosis by providing a measuring means that is disposable about, distal and proximal a stenosis for measuring the dimensions of the tissue in those locations. Moreover, the device is suitable for measuring the working diameter of both healthy and diseased lumen for purposes of accurately determining the dimensions of an appropriate interventional prosthesis.

The device is capable of being introduced into the working channel of a suitable anatomically correct optical scope. For example, a device in accordance with the present invention that is used for nonvascular indications in general and pulmonary indications in particular may be suitably configured for use in the working channel of a bronchoscope. As discussed above, the optical instrument chosen will be a function of the general vascular/nonvascular decision, anatomical location, and physician preference.

Figure 9:
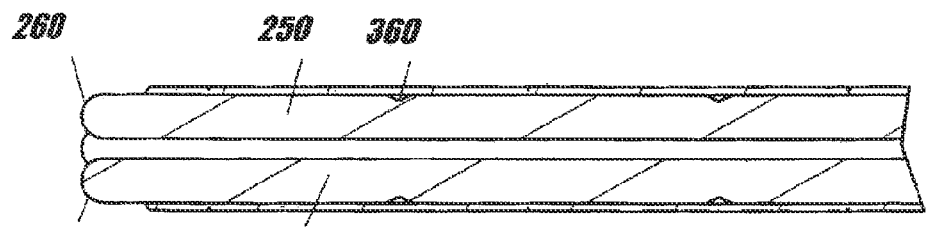
FIG. 9 is a cross sectional view of the legs of the measurement assembly in a closed configuration inside the exterior conduit.
Figure 10:
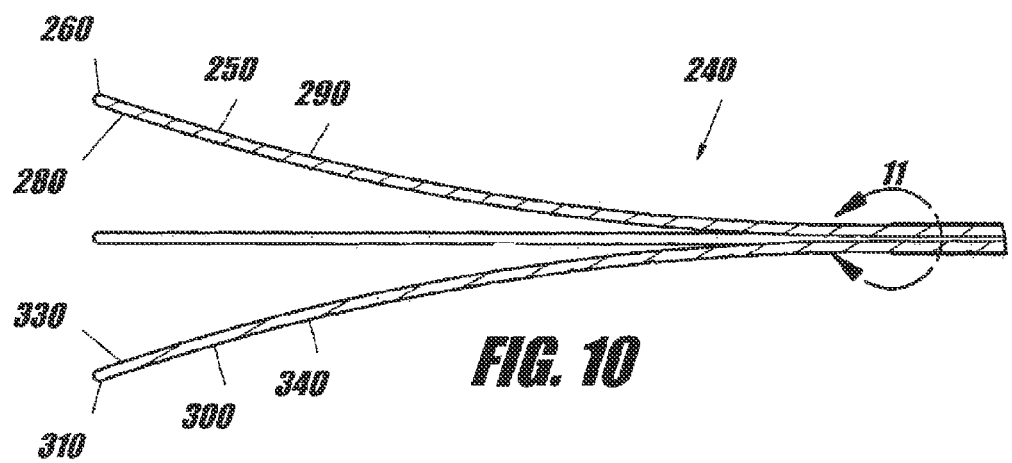
FIG. 10 is a perspective view of the measurement assembly showing the legs in an open configuration, as shown along lines 10-10 of FIG. 6.
Figure 11:
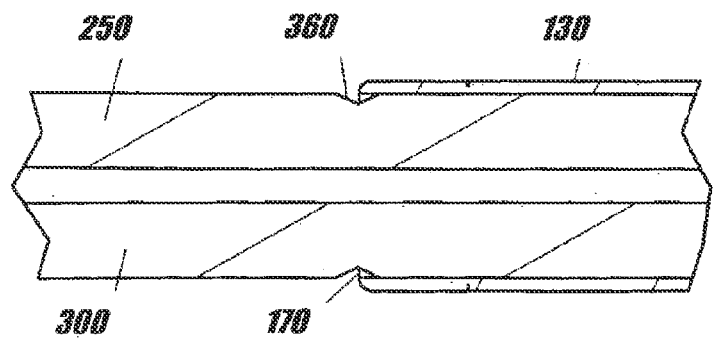
FIG. 11 is a cross sectional view of the distal region of the exterior conduit showing how the detent or lip of the exterior conduit interacts with the corresponding measurement markers on the measurement assembly legs, along lines 11-11.
Figure 13:
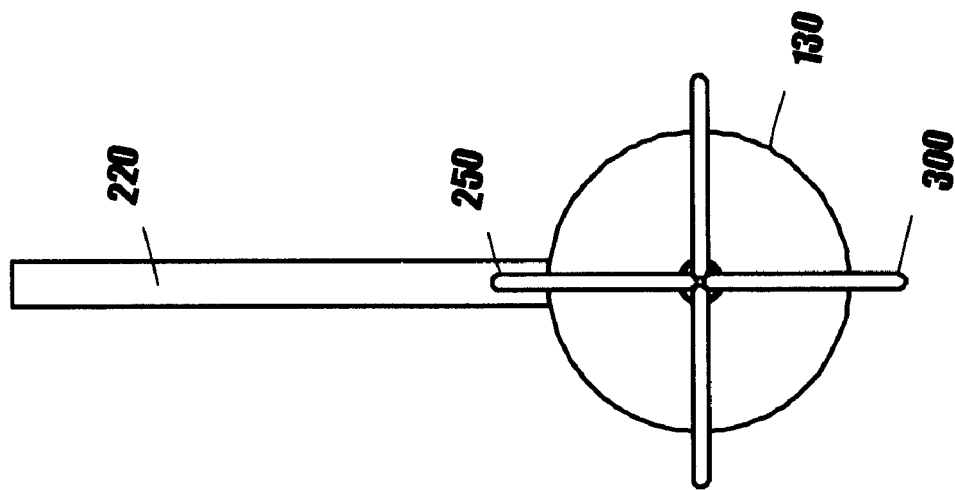
FIG. 13 is a perspective view of the lumen-measuring device of FIG. 1, showing the measurement assembly in the open configuration as viewed from the distal tip thereof.
Figure 12:
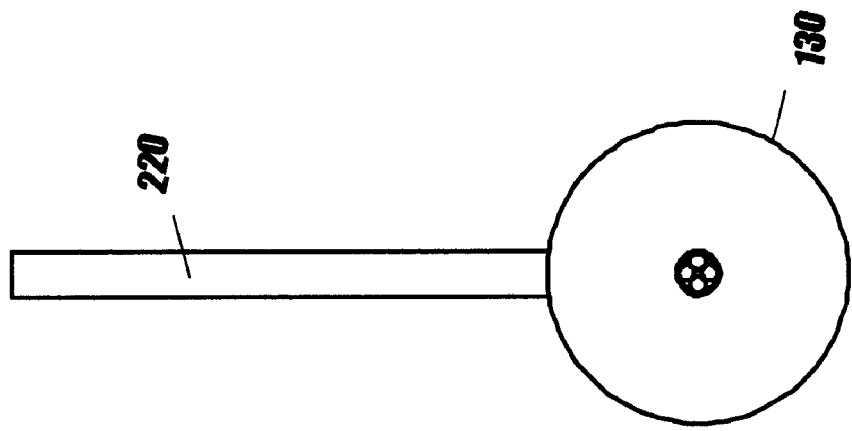
FIG. 12 shows a perspective view of the lumen-measuring device of FIG. 1, showing the measurement assembly in the closed configuration as viewed from the distal tip thereof.

Now making specific reference to the Figures where like numerals refers to like components, a lumen-measuring device is provided to give more accurate lumen dimensional information for purposes of interventional treatment. In particular, a lumen-measuring device 100 is provided generally in FIGS. 1-13.

In a preferred embodiment, the lumen-measuring device 100 comprises a plurality of conduits longitudinally extending between proximal and distal ends, namely exterior 130 and interior 180 conduits, the exterior conduit 130 is coupled with a handle 220 at the proximal end and a measurement assembly 240 at the distal end. The handle 220 and the measurement assembly 240 being operatively connected with one another via the interior conduit 180 at the interior conduit's proximal 190 and distal ends 200, respectively. The interior conduit 180 also has a depth marking mechanism 210 visible through the proximal region of the exterior conduit 140. The handle 220 provides a trigger mechanism 230 that allows the user to place the measurement assembly 240 in an open or closed configuration by pushing or pulling the trigger mechanism 230. The trigger 230 is preferably a slide-gauged mechanism but may be any number of alternative guiding systems known in the art. In the slide gauge embodiment, when the trigger mechanism 230 is pushed in a distal direction with respect to the handle 220, the interior conduit 180 urges the measurement assembly 240 distal the exterior conduit 130 causing the measurement assembly 240 to open. Retracting the trigger mechanism 230 in a proximal direction with respect to the handle 220 closes the measurement assembly 230.

The measurement assembly 230 comprises at least two legs 250, 300 having distal 260, 310 and proximal ends 270, 320 and inward facing 280, 330 and lumen facing 290, 340 surfaces, and the legs are preferably coupled with each other at their respective proximal ends 270, 320. Distal the point at which the legs 250, 300 are coupled, the legs 250, 300 are designed to diverge from one another when unconstrained. In the furtherance of this objective, the legs 250, 300 are preferably formed of a shape memory alloy such as nitinol so that when the legs are constrained by the exterior conduit 130 they lay substantially flush with respect to one another but diverge when the exterior conduit 130 is evacuated.

Additional legs may be employed so that the topology of the lumen 570 may be assessed from varying perspectives. In a preferred embodiment, four legs are provided. Each leg is provided with measurement markers 350 that are disposed at predetermined intervals between the distal and proximal ends of each leg. Accuracy and corresponding leg dimensional measurements can be confirmed and calibrated by providing the lumen-measuring device 100 into a vessel with known interior dimensions. The legs are then urged distally until the distal ends of the legs touch the interior surface of the vessel. Since the interior dimensions of the vessel are known, it is easy to calibrate the measuring device so that the measurement markers correspond to the known dimensions.

As an added feature to ensure accuracy, preferred embodiments of the present device provide legs that have measurement markers 350 that are carved into the legs so as to form detent or lip catches 360. Depending on the embodiment described, markers 350 and lip catches 360 may be used interchangeably as one or both may be present in the same location. The exterior conduit 130 has corresponding detents 170 or a lip 170 about the distal end 150 thereof to ensure that the legs do not overshoot the maximum lumen measurement and damage the lumen tissue. Moreover, only moderate distal force is necessary to urge the legs beyond the lip 170, however, once the proper extension has been achieved, this feature allows the measuring assembly to remain stable until the calculation has been made.

Figure 14:
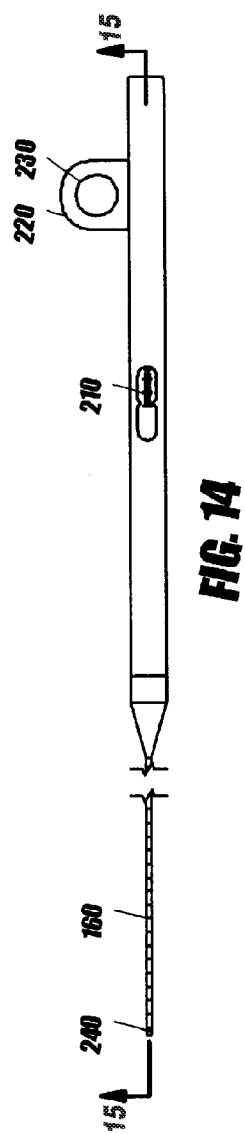
FIG. 14 is a side perspective view of the closed measurement configuration of an alternative lumen-measuring device embodiment showing a measurement indicator through the exterior lumen.
Figure 15:
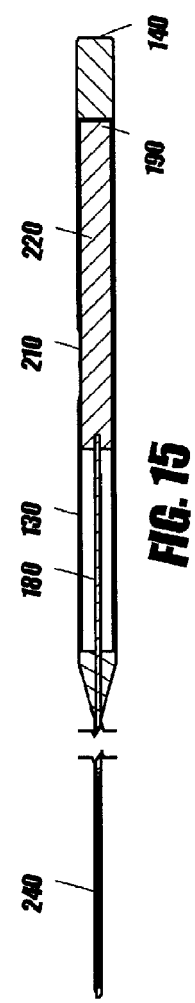
FIG. 15 is a bottom cross-sectional view of the alternative lumen-measuring device of FIG. 14, showing the legs in the closed configuration.

Referring now to FIGS. 14-18, in an alternative embodiment, instead of the distal ends of the legs making independent contact with the lumen surface, the distal ends are coupled together so that measurement takes place proximal the distal ends of the legs. In this embodiment, the measurement assembly takes on the configuration of a whisk, wherein the exterior diameter at the distal and proximal ends, when fully extended, is significantly smaller relative to the measurement portion therebetween. However, when the measurement assembly is retracted, the legs are relaxed and reside adjacent one another so that the legs may be retracted within the exterior conduit.

In this and other related embodiments, the exterior conduit has measurement markers 160 formed thereon. Additionally, the lumen facing surfaces 290, 340 of the measurement assembly 240 legs have measurement markers 350 and/or 360 formed thereon. As the trigger mechanism 230 is pushed distally, the measurement assembly 240 moves distal the distal end 150 of the exterior conduit 130 and begins to separate the legs of the measurement assembly 240 with respect to one another. The further the trigger mechanism 230 is pushed in the distal direction, the further the legs open and the greater the number of measurement markings 350 and/or 360 on the measurement assembly 240 extended beyond the distal end 150 of the exterior conduit 130. In a preferred embodiment, the distal end 150 of the exterior conduit 130 has inward facing detents or lip 170 that are complementary to the measurement markers 350 and/or 360 on the measurement assembly 240. At each measurement marking 350, the detent or lip 170 may be engaged by the detent catches 360 of the measurement markers 350 to prevent overshooting the target. Once the legs have been opened until the distal ends of the legs of the measurement assembly 240 are in contact with the tissue to be measured, the user need only count the measurement markings 350 to determine the dimensions of the target tissue.

In order to determine the length of the target tissue, the user need only open the measurement assembly 240 just proximal and just distal the target tissue, in no particular order and note the distances between the two locations on the depth marking mechanism 210 of the interior conduit 180, which is preferably just distal the handle 220.

Figure 23:
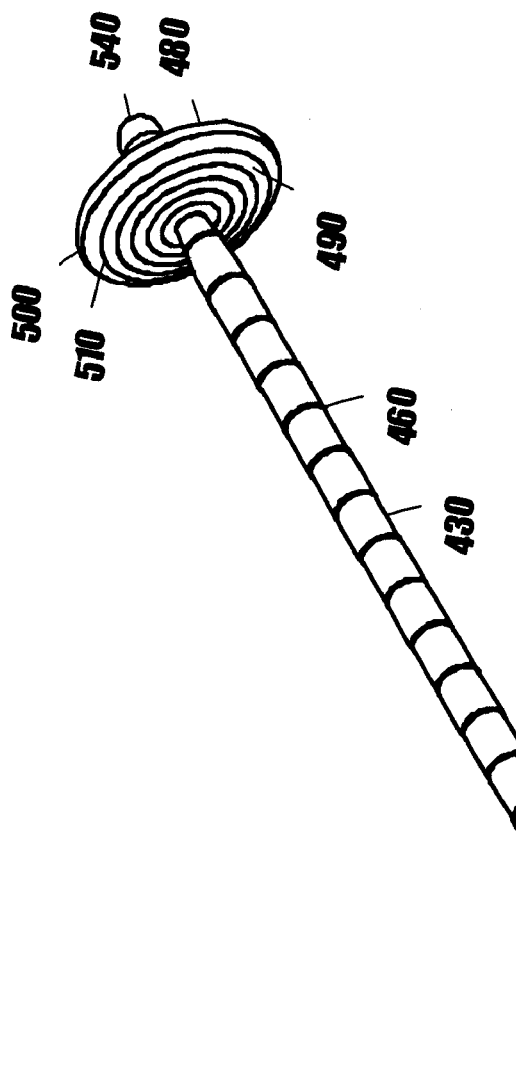
FIG. 23 is a perspective view of the measuring portion of the lumen-measuring device of FIG. 19, showing the measurement markers on the diameter measurement balloon in the inflated configuration.
Figure 24:
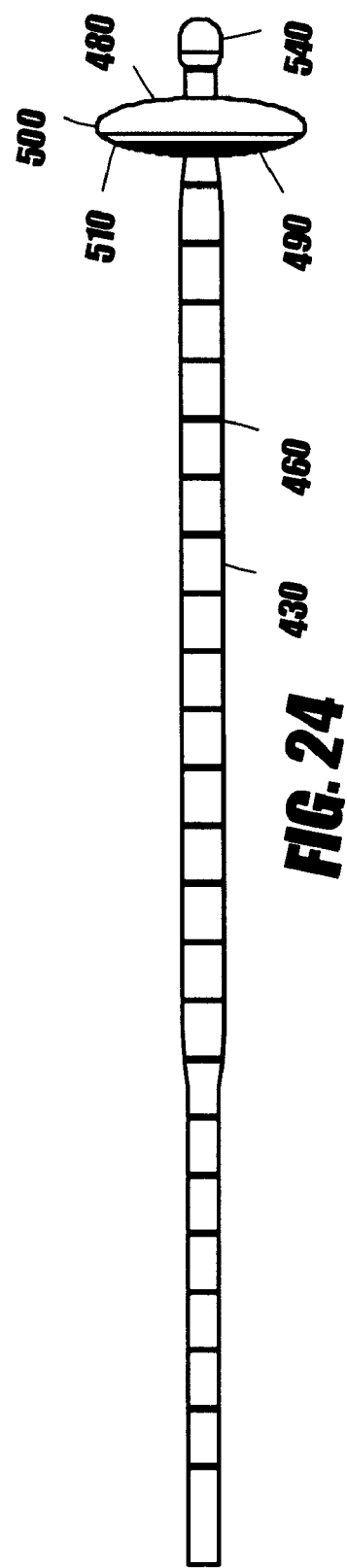
FIG. 24 is a side view of the measuring portion of the lumen-measuring device of FIG. 19, showing the measurement markers on the diameter measurement balloon in the inflated configuration.

An alternative embodiment of the present invention, as shown specifically in FIGS. 19-30 comprises a flexible device 420 with preferably two balloons and three conduits—one conduit for each balloon and one that goes all the way through the device 420. The distal balloon, when inflated, is substantially round in the radial direction when viewed along the longitudinal axis of the device 420, and is referred to generally as the diameter measurement balloon 470; the proximal balloon is longer and is referred to generally as the dilation balloon 430. A first conduit 520 preferably inflates the diameter measurement balloon 470 and a second conduit 550 inflates the dilation balloon 430. A third conduit 560, which preferably terminates at the distal end tip 540, principally serves a delivery and measurement function. In a preferred embodiment, the outer tube of device 420 has measurement markings 530 that are visible from the interior and/or the exterior thereof.

The diameter measurement balloon 470 has substantially flat distal 480 and proximal 490 surfaces, with a substantially circular edge 500 therebetween, resulting in a hollow pancake shaped configuration, when inflated. In a preferred embodiment, the diameter measurement balloon 470 has diameter measurement marker 510 of varying colors on the proximal and/or distal surface thereof to form a target-like representation. Alternatively, the dilation balloon 430 has a substantially cylindrical shape with proximal 450 and distal ends 440 coupled along the outer tube of device 420.

When the pre-sterilized device is initially installed the diameter measurement balloon 470 is compressed proximal the distal tip 540 of the outer tube of device 420 and the dilation balloon 430 is compressed about the outer tube of device 420, proximal the diameter measurement balloon 470. In this configuration, as specifically shown in FIGS. 27-28, the device is easily delivered to the target site. When used to evaluate stenotic tissue, the tip 540 is preferably positioned distal the stenosis 580 such that the diameter measurement balloon is placed just distal the stenosis. The diameter measurement balloon 470 is then inflated sufficiently to allow it to sit flush with the inner diameter of the subject lumen 570 or stenosis 580.

Through the use of visualization means, such as optical instruments like a bronchoscope 110, the topology of the stenosis 580 can be directly viewed. The diameter measurement balloon 470 is preferably designed with diameter measurement markers 510 formed on the proximal face thereof to allow the user to visually measure the extent of luminal occlusion based on the number of diameter measurement markers covered by the stenosis 580 when viewing the diameter measurement balloon 470 from a position proximal the stenosis 580. Furthermore, this allows the physician to see if the stenosis 580, or other observed occlusion, is symmetrical, etc.

Simultaneously, the physician may observe the measurement markers 460, 510 visible on the outer tube of device 420 and surface of diameter measurement balloon 470 to see the dimensions of the occlusion from end-to-end or from specific points. Additionally, the dilation balloon 430 may also be inflated to serve as an additional measurement of the working diameter of the diseased lumen 570. To this end, the dilation balloon 430 is inflated until it substantially closes the diseased portion of the lumen 570.

Based on the measurements collected from this simple and inexpensive procedure, an interventional prosthesis may be selected, if necessary, that is appropriate in length and diameter so as to prevent further damage to the target lumen while providing sufficient outward radial support.

In this and other embodiments that employ balloons, a predetermined air pressure is provided to each balloon and each balloon conduit may be configured with a pressure manometer.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

The invention claimed is:

1. A device that is configured to allow a user to measure a diameter of a body lumen, the device comprising:
    a diameter measurement balloon comprising distal and proximal surfaces, the diameter measurement balloon having concentric diameter measurement markers on the proximal and/or distal surface thereof;
    a dilation balloon that is configured to radially expand to dilate a stenosis within the body lumen; and
    a plurality of conduits, comprising: a diameter measurement conduit for inflating the diameter measurement balloon, and a dilation conduit for inflating the dilation balloon.

2. The device of claim 1, wherein the plurality of conduits are co-extruded.

3. The device of claim 1, further comprising an optical scope.

4. A method of measuring a diameter of a target segment of a lumen of a patient, the method comprising:
    providing a measuring device, comprising:
        a diameter measurement balloon comprising distal and proximal surfaces, the diameter measurement balloon having concentric diameter measurement markers on the proximal and/or distal surface thereof;
        a dilation balloon that is configured to radially expand to dilate a stenosis within the body lumen; and
        a plurality of conduits, comprising: a diameter measurement conduit for inflating the diameter measurement balloon, and a dilation conduit for inflating the dilation balloon;
    introducing the device into an appropriate anatomical orifice of the patient;
    delivering the device adjacent the target segment of the lumen within the patient; and
    measuring the diameter of the target segment of the lumen within the patient.

5. The method of claim 4, wherein the measuring device further comprises an optical scope operatively coupled therewith, such that the measuring step is accomplished utilizing the optical scope.

6. The method of claim 4, wherein the target segment of the lumen is stenotic.

7. The method of claim 4, further comprising measuring another dimension of the target segment, wherein the dimension is selected from the group consisting of length, height, and circumference.

8. A device that is configured to allow a user to measure a diameter of a body lumen, the device comprising:
    a diameter measurement balloon comprising smooth distal and proximal surfaces, the diameter measurement balloon having diameter measurement markers on the proximal and/or distal surface thereof;
    a dilation balloon that is configured to radially expand to dilate a stenosis within the body lumen; and
    a tube having an interior and an exterior, the interior defining three conduits passing at least partially therethrough, the first conduit comprising a diameter measurement conduit for inflating the diameter measurement balloon, the second conduit comprising a dilation conduit for inflating the dilation balloon and a third conduit that extends the length of the tube.

9. The device of claim 8, wherein the tube further comprises proximal and distal ends and measurement markings therebetween.

10. The device of claim 8, further comprising an optical scope.

11. A method of measuring a diameter of a target segment of a lumen of a patient, the method comprising:
    providing a measuring device, comprising:
        a diameter measurement balloon comprising smooth distal and proximal surfaces, the diameter measurement balloon having diameter measurement markers on the proximal and/or distal surface thereof;
        a dilation balloon that is configured to radially expand to dilate a stenosis within the body lumen; and
        a tube having an interior and an exterior, the interior defining three conduits passing at least partially therethrough, the first conduit comprising a diameter measurement conduit for inflating the diameter measurement balloon, the second conduit comprising a dilation conduit for inflating the dilation balloon and a third conduit that extends the length of the tube;
    introducing the device into an appropriate anatomical orifice of the patient;
    delivering the device adjacent the target segment of the lumen within the patient; and
    measuring the diameter of the target segment of the lumen within the patient.

12. The method of claim 11, wherein the measuring device further comprises an optical scope operatively coupled therewith, such that the measuring step is accomplished using utilizing the optical scope.

13. The method of claim 11, wherein the target segment of the lumen is stenotic.

14. The method of claim 11, further comprising measuring another dimension of the target segment, wherein the dimension is selected from the group consisting of length, height, and circumference.

* * * * *